US009788551B2

(12) United States Patent
Lüth

(10) Patent No.: US 9,788,551 B2
(45) Date of Patent: Oct. 17, 2017

(54) LIQUID PREPARATION FOR BIOLOGICAL PLANT PROTECTION, METHOD FOR PRODUCING IT AND USE THEREOF

(75) Inventor: Peter Lüth, Wismar (DE)

(73) Assignee: Bayer CropScience Biologies GmbH, Malchow/Poel Island (DE)

( * ) Notice: Subject to any disclaimer, the term of this patent is extended or adjusted under 35 U.S.C. 154(b) by 160 days.

(21) Appl. No.: 14/119,825

(22) PCT Filed: May 18, 2012

(86) PCT No.: PCT/DE2012/000523
§ 371 (c)(1),
(2), (4) Date: Feb. 5, 2014

(87) PCT Pub. No.: WO2012/163322
PCT Pub. Date: Dec. 6, 2012

(65) Prior Publication Data
US 2014/0212387 A1    Jul. 31, 2014

(30) Foreign Application Priority Data

May 27, 2011    (DE) .................. 10 2011 102 632

(51) Int. Cl.
*A01N 63/00* (2006.01)
*A01N 63/04* (2006.01)
*A01N 65/00* (2009.01)

(52) U.S. Cl.
CPC .............. *A01N 63/04* (2013.01); *A01N 63/00* (2013.01)

(58) Field of Classification Search
None
See application file for complete search history.

(56) References Cited

U.S. PATENT DOCUMENTS

| | | | |
|---|---|---|---|
| 6,117,816 A | 9/2000 | Jimoh et al. | |
| 7,968,107 B2 | 6/2011 | Baur et al. | |
| 8,293,733 B2* | 10/2012 | Casana Giner | A01N 43/40 514/229.2 |
| 2002/0072474 A1 | 6/2002 | Bickers et al. | |
| 2005/0069567 A1 | 3/2005 | Ballard et al. | |
| 2006/0276339 A1* | 12/2006 | Windsor | A01N 25/32 504/127 |
| 2007/0141032 A1 | 6/2007 | Matsumura et al. | |
| 2007/0281860 A1 | 12/2007 | Baur et al. | |
| 2009/0035280 A1 | 2/2009 | Kimura et al. | |
| 2009/0054238 A1 | 2/2009 | Fleute-Schlachter et al. | |
| 2009/0099135 A1* | 4/2009 | Enan | A01N 65/00 514/86 |
| 2011/0145950 A1* | 6/2011 | Nguyen | C12N 15/8205 800/294 |

FOREIGN PATENT DOCUMENTS

| | | |
|---|---|---|
| DE | 100 36 003 | 2/2002 |
| DE | 10 2004 011 007 | 9/2005 |
| JP | H07258015 A | 10/1995 |
| JP | 2005-206486 A | 8/2005 |
| WO | WO 00/22149 * | 4/2000 ............. C12N 15/82 |

OTHER PUBLICATIONS

Joh et al., Biotechnol. Prog., 22: 723-730 (2006).*
Simmons et al., Biotechnol. Lett., 29:641-645 (2007).*
Simmons et al., Biotechnol Bioeng., 102(3) 965-970 (2009).*
VanderGheynst et al., Biomass Bioenergy, 32:372-379 (2008).*
Sanchez translation (2010).*
van den Berg et al., S. Afr. J. Plant Soil, 24(3):172-175 (2007).*
ATCC, Tech Bulletin 2 (2011).*
Perkins. How to preserve stocks, <http://www.fgsc.net/neurosporaprotocols/HowtopreservestocksK%20final.pdf> Oct. 10, 2005 (Accessed Jul. 19, 2016).*
Gatarayiha et al., Exp. Appl. Acarol., 50:217-229 (2010).*
Akbar et al., "Efficacy of Beauveria Bassiana for Red Flour Beetle When Applied With Plant Essential Oils or in Mineral Oil and Organosilicone Carriers," Journal of Economic Entomology, vol. 98, No. 3, pp. 683-688, (Jun. 1, 2005).
Gatarayiha et al., "Effects of Adjuvant and Conidial Concentration on the Efficacy of Beauveria Bassiana for the Control of the Two Spotted Spider Mite, Tetranychus Urticae," Experimental and Applied Acarology, vol. 50, No. 3, pp. 217-229, (Sep. 18, 2009).
Hatting et al., "Efficacy of Beauveria Bassiana (Hyphomycetes) for Control of Russian Wheat Aphid (Homoptera: Aphididae) on Resistant Wheat Under Field Conditions," Biocontrol Science and Technology, vol. 14, No. 5, pp. 459-473, (Aug. 1, 2004).
Gatarayiha et al., "Effects of Crop Tyhpe on Persistence and Control Efficacy of Beauveria Bassiana Against the Two Spotted Spider Mite," Biocontrol, vol. 55, No. 6, pp. 767-776, (Jun. 20, 2010).
Sanchez et al, "Evaluation of Entomopatogenic Fungi Under Lab Conditions to Control the *Macadamia Pest Antiteuchus* SP. ," pp. 1-16, (Nov. 25, 2010) retrieved from URL:http://www.oriusbiotecnologia.com/resultados-investigacion-aplicada-a-desarrollo/101-macadamia, (retrieved on Sep. 27, 2012) .
Lindow et al., "Management of Frost Injury, Fire Blight, and Fruit Russeting of Pear Using Biological and Cultural Methods," Department of Plant and Microbiology, University of California Berkely, CA, pp. 1-7, (Oct. 1, 2007) retrieved for URL:http//www.calpear.com/_pdf/research-reports/05reports/1_plant.pfd, (retireved Sep. 26, 2012).
Bazilah et al., "Effect of Carrier and Temperature on the Viability of *Burkholderia* SP. (UPMB3) and *Pseudomonas* SP. (UPMP3) During Storage," International Journal of Agriculture & Biology, pp. 198-202, (Apr. 1, 2011).

(Continued)

*Primary Examiner* — Thomas J Visone

(57) ABSTRACT

The invention relates to a liquid preparation comprising biologically active fungi and/or fungal organs and/or other microorganisms in a suspension, to a method for producing it and to the use thereof for biological protection of plants, for biological plant strengthening, or for biological soil improvement. Polyether-modified trisiloxane is a preferred liquid used. The preparation according to the invention is notable for easily manageable storage at room temperature, trouble-free transport, and simplicity of production and application.

12 Claims, No Drawings

(56) References Cited

OTHER PUBLICATIONS

Tittabutr et al., "Growth, Survival and Field Perormance of Bradyrhizobial Liquid Inoculant Formulations With Polymeric Additives", Scienceasia, vol. 33, No. 1, pp. 69-77, (Jan. 1, 2007).
Albrareda et al., "Alternatives to Peat As a Carrier for Rhizobia Inoculants: Solid and Liquid Formulations," Soil Biology and Biochemistry, vol. 40, No. 11, pp. 2771-2779, (Nov. 1, 2088).
Kuecuek et al., "Effect of Formulation on the Viability of Biocontrol Agent, Trichoderma Harzianum Conidia," African Journal of Biotechnology, pp. 483-486, (Jun. 1, 2005).
Torres et al., "Liquid Formulation of the Biocontrol Agent Candida Sake by Modifying Water Activity or Adding Protectants," Journal of Applied Microbiology, vol. 94, No. 2, pp. 330-339 (Jan. 1, 2003).
"Break-Thru S240," pp. 1-2, (Mar. 1, 2009) retrieved from URL:http://ww.break-thru.com/sites/dc/downloadcenter/Evonik/Product/BREAK-THRU/break-thru-s-240.pdf (retrieved Sep. 25, 2012).
Alves et al., "Effects of Different Formulations on Viability and Medium-Term Storage of Metarhizium Anisopliae Conidia," Neotropical Entomology, vol. 31, No. 1, pp. 91-99 (Jan. 1, 2002).
Moore et al., "Long-Term Storage of Metarhizium Flavoviride Condia in Oil Formulations for The Control of Locusts and Grasshoppers," Biocontrol Science and Technology, pp. 193-199, (Jan. 1, 1995).
Roy et al., "Bizarre Interactions and Endgames: Entomopathogenic Fungi and Their Arthropod Host," Annual Review of Entomology, vol. 51, No. 1, pp. 331-357, (Jan. 1, 2006).
International Search Report for PCT/DE2012/00523 Mailed Oct. 8, 2012.
"CAS-No. 134180-76-0, Break Thru S240" In: "CAS-No. 134180-76-0, Break Thru S240", Jun. 14, 1991 (Jun. 14, 1991), Chemical Abstracts Service, U.S.A., XP055231227, Seiten 1-3.
Anderson, G., et al., "Determination of Product Shelf Life and Activation Energy for Five Drugs of Abuse," Clin. Chem, 1991, vol. 37, No. 3., pp. 398-402.
Larena, I., et al., "Effects of Stabilizers on Shelf-Life of Epicoccum nigrum Formulations and Their Relationship with Biocontrol of Postharvest Brown Rot by Monilinia of Peaches," Journal of Applied Microbiology, 2007, vol. 102, pp. 570-582.

\* cited by examiner

LIQUID PREPARATION FOR BIOLOGICAL PLANT PROTECTION, METHOD FOR PRODUCING IT AND USE THEREOF

CROSS REFERENCE TO RELATED APPLICATIONS

This application is a §371 National Stage Application of PCT/DE2012/000523, filed May 18, 2012, which claims priority to German Application No. 10 2011 102 632.4, filed May 27, 2011.

BACKGROUND OF THE INVENTION

Field of the Invention

The invention relates to a liquid preparation, to methods for the production thereof and to the use thereof. The area of application is agriculture and forestry, including horticulture and pomiculture and also the cultivation of ornamental plants, and the establishment and maintenance of lawns. In this regard, the goal of the invention is, in particular, biological plant protection, biological plant strengthening and biological soil improvement.

Description of Related Art

The use of preparations based on the basis of microscopic fungi or other microorganisms allows biological plant protection and thus preventive or curative control of plant disease-causing organisms and harmful organisms on the basis of ecological mechanisms of action directed against said disease-causing and harmful organisms.

Other microorganisms, such as *Trichoderma* spp., *Pythium oligandrum*, *Bacillus* spp., *Pseudomonas* spp. and *Streptomyces* spp., are capable of causing reactions in the plants which lead to increased resistance against disease-causing organisms or other stress factors, such as dryness, poor supply of nutrients, unfavorable pH levels or high salt content in the soil.

Yet further microorganisms, such as *Trichoderma* spp., *Penicillium bilaii*, *Azotobacter* spp., *Azotomonas* spp., *Azospirillum* spp. and *Rhizobium* spp., lead to an improvement in nutrient availability in the soil or directly at the plant root.

Such preparations are environmentally friendly and make use of natural regulatory mechanisms which have developed in nature over the course of evolution.

The literature discloses various formulations or preparations in which fungal microorganisms constitute agents in biological plant protection agents, biological plant strengthening agents and biological fertilizers. For instance, microorganisms are formulated as, for example, water-dispersible granules (WG), water-dispersible powders (WP), oil dispersions (OD) or suspension concentrates (SC) (Anonymous, 2005).

The formulation has to ensure that the products have a good shelf life. This means that the microorganisms should be able to retain their vitality for as long as possible even at high temperatures.

The products should have good solubility/dispersibility in water, so that use can be carried out by means of spray application or with the aid of the irrigation system and the microorganisms (e.g., fungal spores or bacterial cells) can be well distributed in the soil, on the plant or on the harmful organism. In this connection, it is particularly important that the microorganisms are not clumped together in aggregates in the aqueous suspension to be used, but instead occur individually (e.g., fungal spores or bacterial cells swimming separately from one another in a suspension). If aggregates occur in the aqueous suspension to be used, this may lead to clogging of the nozzles of the plant protection sprayer or the distribution of the active biological substance in the soil, on the plant or on the harmful organism is inhomogeneous, adversely affecting the action of the product.

Particularly microorganisms which need to be watered into the soil for full development of their action (e.g., for controlling nematodes, soil insects or soil-borne disease-causing organisms) lose their action, since they are already filtered out in the uppermost soil layers by the soil structure if relatively large aggregates are present in the use suspension.

Various microorganisms or organs of microorganisms, more particularly fungal conidia of the genera *Beauveria*, *Isaria*, *Nomuraea*, *Metarhizium*, *Paecilomyces* and *Penicillium*, are water-repellent. In some cases, this property of the microorganisms additionally hampers their use. They can be poorly suspended in water, poorly distributed on the surface of plants or harmful insects, and watered into the soil with difficulty.

The disadvantage of some water-dispersible powders is that the outflow of dusts during their use can be prevented only with difficulty, and so contamination of the user or of the environment can occur.

Because of their formulation, many microbiological preparations contain only a small quantity of their active agent. For instance, there are preparations which contain only $1\times10^7$ or $1\times10^8$ live fungal conidia per gram. In the case of a minimum application amount which is required for a good action and which is in many cases $1\times10^{11}$ or $1\times10^{12}$ and more fungal conidia per hectare, the small active substance concentration in the preparations brings about high costs (costs relating to manufacture, storage, transport and use).

Live microorganisms differ from chemically synthesized active substances with respect to, inter alia, shelf life, since they are not stable in conventional solvents used. If they are exposed to unfavorable conditions, they lose their germination capacity and die. This occurs under prolonged storage, during incubation under relatively high temperatures, upon contact with chemical substances and the like.

SUMMARY

It is therefore an object of the invention to develop a liquid preparation containing an active microorganism or its organs, for example fungal spores, fungal conidia, chlamydospores, sclerotia, segments of fungal hyphae, bacterial cells or viruses. It shall be storable over a prolonged period (at least 12 months) with little technical effort and with maintenance of its vitality and aggressiveness at a relatively high temperature. Furthermore, it shall be easily suspendable in water and easily distributable on the plant, the target organism or in the soil. The liquid preparation shall also be highly concentrated.

DETAILED DESCRIPTION OF A PREFERRED EMBODIMENT

The invention is realized according to claim 1. Further advantageous designs, aspects and details of the invention are revealed by the dependent claims, the description and the examples.

The starting point of the invention is the surprising finding that the mixing of live microorganisms or their organs into polyether-modified trisiloxane leads to such a liquid preparation. It has additionally been found that, surprisingly, live microorganisms mixed into, i.e., suspended in, polyether-modified trisiloxane keep their vitality. It has additionally been found to be particularly surprising that the suspended live microorganisms keep their vitality during storage for 12 months. Exceptionally surprising was also the fact that fungal spores can be suspended in 100% strength polyether-modified trisiloxane without dying off as a result. Even more surprising was the fact that the storage life of the spores is actually improved through the suspension in a polyether-modified trisiloxane.

The suspension of the microorganisms or their organs in polyether-modified trisiloxane produces a dispersion concentrate (DC). In this regard, the liquid preparation according to the invention is characterized by a suspension consisting of a biologically active microorganism or organs of a microorganism, for example fungal spores, fungal conidia, chlamydospores, sclerotia, segments of fungal hyphae, bacterial cells or viruses, and polyether-modified trisiloxane.

The invention is advantageous because the storage life of the biological plant protection agent is decisively improved over the products of the prior art. The invention is also advantageous because the water-repellent microorganisms or parts thereof can be suspended substantially more effectively in pure polyether-modified trisiloxane than in water, and so, in contrast to aqueous solutions, clumping of the microorganisms does not occur. If dissolution/suspension of the product in water is to be carried out for use, these properties remain preserved, and so the microorganisms or organs of microorganisms can be uniformly distributed on the plants or in the soil. A further advantage of the invention is that the microorganisms, or the parts thereof, suspended in pure polyether-modified trisiloxane can be mixed well with water and thus various use concentrations are obtainable.

It is known from the literature that, for example, fungal spores in aqueous suspensions are used with the use of polyether-modified trisiloxane, as contained in the products Silwet or Break-Thru for example (Akbar et al., 2005; Gatarayiha et al., 2010; Legaspi et al., 2000; Wekesa et al., 2005). Here, however, the polyether-modified trisiloxane is only mixed into the water or the aqueous conidia suspension immediately prior to the use of the conidia in order to improve the applicability of the conidia. The polyether-modified trisiloxane thus merely serves as a wetting agent and/or adhesive agent. The use of nonionic surfactants is also mentioned in DE102004011007, but only in the context of an oil-based formulation and not as pure surfactants. Polyether-modified trisiloxanes in the form of nonionic surfactants are used in plant protection agents, though for suspending chemically synthesized active substances (DE10036003A1, U.S. Pat. No. 6,117,816A). However, it was hitherto unknown that microorganisms or their organs can be formulated in a pure polyether-modified trisiloxane and stored in a vital state over a prolonged period. Furthermore, a biological plant protection agent consisting of a formulation of live microorganisms as active agent in a pure polyether-modified trisiloxane is hitherto unknown.

The invention provides in particular a liquid preparation for biological plant protection comprising a suspension consisting of an active microorganism or a mixture of multiple active microorganisms or organs of microorganisms and of a polyether-modified trisiloxane.

In this regard, it is preferable for the active microorganism or the mixture of active microorganisms or the organs of the active microorganism(s) in the liquid preparation according to the invention to have an antagonistic and/or hyperparasitic action directed against particular plant disease-causing organisms. It is additionally preferable for the active microorganism or the mixture of active microorganisms or the organs of the active microorganism(s) in the liquid preparation according to the invention to have a resistance-inducing action and/or stress tolerance-inducing action which manifests itself on plants or a nutrient availability-increasing action.

According to the invention, preferred active microbiological substances in the liquid preparation according to the invention are a fungus, multiple fungi or a mixture of various fungal species. If organs of fungi are used, then according to the invention they may preferably be spores, conidia, blastospores, chlamydospores, sclerotia or hyphae segments or a mixture of said organs. In this regard, the use of the following fungi having antagonistic action against particular plant disease-causing organisms is particularly preferred:

*Ampelomyces quisqualis*
*Beauveria bassiana*
*Beauveria brongniartii*
*Clonostachys rosea*
*Coniothyrium minitans*
*Gliocladium catenulatum*
*Isaria* spp.
*Laetisaria arvalis*
*Lecanicillium lecanii*
*Lecanicillium muscarium*
*Metarhizium anisopliae*
*Nomuraea rileyi*
*Paecilomyces lilacinus*
*Phoma macrostoma*
*Pythium oligandrum*
*Talaromyces flavus*
*Teratosperma oligocladum*
*Trichoderma* spp.
*Verticillium biguttatum*

Preferably used as fungi which improve nutrient availability in the soil and/or increase the resistance of plants to stress factors (including disease-causing and harmful organisms) are:

*Penicillium bilaii, Trichoderma* spp. and all species which can be classified in the group of mycorrhizal fungi.

Additionally preferred according to the invention is a liquid preparation in which the active microbiological substance is a bacterium or a mixture of various bacteria. In this regard, particular preference is given to the use of bacteria which improve nutrient availability in the soil and/or increase the resistance of plants to stress factors (including disease-causing and harmful organisms). The following bacteria are preferably used:

*Bacillus* spp., *Pseudomonas* spp., *Streptomyces* spp., *Azotobacter* spp., *Azotomonas* spp., *Azospirillum* spp. and *Rhizobium* spp.

Other bacteria are discussed or already used as active agents in biological plant protection agents. Examples of these include: *Bacillus* spp., *Serratia* spp., *Pseudomonas* spp., *Streptomyces* spp., *Pasteuria* spp. and *Burkholderia* spp.

Additionally preferred according to the invention is a liquid preparation in which the active microbiological substance is a virus or a mixture of various viruses.

Additionally preferred according to the invention is a liquid preparation in which the active microbiological substance is a mixture of the aforementioned fungi, bacteria or viruses or a mixture of, in each case, two of these microorganisms.

The liquid preparation according to the invention is produced as follows:

The biologically active microorganism is cultured on a growth medium suitable for this purpose according to methods known per se, for example submerged fermentation or solid-state fermentation. Following culturing, the microorganism or its preferably used organs is separated from the culture substrate. In a particular variant, the culture substrate covered by the microorganism (especially when using solid culture substrates) is dried beforehand. Alternatively, the microorganism or its preferably used organs can be dried, for example with the aid of freeze-drying, after its separation from the culture substrate. After the separation and optional drying, the microorganism or its preferably used organs is suspended in a polyether-modified trisiloxane. The trisiloxane has preferably been modified with propylene glycol n-butyl ether (PnB), CAS No. 29387-86-8 (5131-66-8)
dipropylene glycol n-butyl ether (DPnB), CAS No. 29911-28-2 (35884-42-5)
dipropylene glycol methyl ether acetate (DPMA), CAS No. 88917-22-0
tripropylene glycol methyl ether (TPM), CAS No. 25498-49-1 & 20324-33-8
- propylene glycol methyl ether (PM), CAS No. 107-98-2
- propylene glycol methyl ether acetate (PMA), CAS No. 108-65-6
- dipropylene glycol methyl ether (DPM), CAS No. 34590-94-8 tripropylene glycol monomethyl ether.

Particular preference is given to the polyether-modified trisiloxane Break-Thru, and very particular preference is given to the polyether-modified trisiloxane S240, CAS No. 134180-76-0, with the chemical name oxirane, methyl-, polymer with oxirane, mono(3-(1,3,3,3-tetramethyl-1-((trimethylsilyl)oxy)disiloxanyl)propyl) ether.

Before the separation of the microorganism or its preferably used organs, culturing is optionally followed by processing of the covered culture substrate by means of an appropriate dispersion method or, after drying, by means of an appropriate milling method. The separation of the microorganism or its preferably used organs is then subsequently achieved by methods known per se, such as sieving, filtration, air-classification, decantation or centrifugation methods.

According to the invention, the liquid preparation is used as a biological plant protection agent, biological plant strengthening agent or biological soil improvement agent, and if necessary it is diluted with water to the use concentration depending on the intended use. The preparation can be mixed or watered into the soil, applied directly to the plants, or used for seed treatment.

For instance, the preparation can be used with the conidia of *Paecilomyces lilacinus* as active agent for the biological control of plant-parasitic nematodes. In the case of use of spores of *Talaromyces flavus*, the preparation can be used to control *Verticillium dahliae*, a disease-causing organism which brings about economically significant wilting in cotton. In the case of use of spores of *Nomuraea rileyi*, the preparation can be used to control the caterpillars of various harmful butterfly species, such as *Helicoverpa armigera* and *Spodoptera exigua*. Use of the preparation with the use of the conidia of *Penicillium bilaii* increases the availability of mineral phosphorus in the soil.

The liquid preparation according to the invention has a long storage life at room temperature and is completely soluble in water, with the active microbial agent being suspended in the water/polyether-modified trisiloxane solution.

For instance, after twelve-month storage of the preparation at room temperature, it was still possible to determine 92.3% vitality of the conidia of *P. lilacinus*. The action of the preparation was still sufficient to distinctly reduce the population of the nematode *Meloidogyne incognita* in the soil. For this reason, the preparation is highly suitable for commercial use.

The preparation is stored and transported in the absence of air in bottles, bags, canisters or drums which have been sealed airtight.

Application is simple owing to the good water solubility of the preparation and associated good suspendability of the microorganism or its preferably used organs in the spray liquid and can be carried out by means of spray methods or by injection into the irrigation system, ensuring uniform distribution of the active agent in the soil, on the plant or on the harmful organisms to be controlled.

In summary, it is determined that the preparation according to the invention is notable for easily manageable storage at room temperature, problem-free transport, simple manufacture and use.

The invention will now be more particularly elucidated using exemplary embodiments, which, however, are not intended to restrict the invention.

Example 1

The fungus *Paecilomyces lilacinus* was cultured on a suitable solid substrate under axenic conditions. After culturing, the culture substrate with the fungal conidia situated thereon was dried.

The conidia were then separated from the dry culture substrate with the aid of an air-classification and filtration method. At this time, they contained residual moisture of 8.3%. 80 g of the dried conidia powder, which had a concentration of $2.8\times10^{11}$ conidia per gram, were suspended in 100 ml of polyether-modified trisiloxane, commercial preparation Break-Thru s240. The resulting liquid preparation contained $1.41\times10^{11}$ conidia per milliliter and $1.37\times10^{11}$ live conidia per milliliter. This corresponds to a concentration of live conidia in the liquid preparation of 97.24%.

The liquid preparation was incubated at room temperature (20-22° C.), and the germination capacity of the conidia of *Paecilomyces lilacinus* was determined monthly. To investigate the germination capacity, samples were taken regularly, mixed with water in a ratio of 1:10 000, incubated for 5 hours in this mixture, and spread out in 0.1 ml on a suitable agar growth medium. The agar plates were then incubated at 25° C. for 24 hours and then examined under a microscope. In this examination, the number of germinated conidia, which are clearly identifiable by the formation of a germ tube, was determined and related to the number of nongerminated conidia. The results of the counts are shown in the table below.

TABLE 1

Storage life of the liquid formulation according to the invention of the conidia of *Paecilomyces lilacinus*

| Storage time | Germinated conidia (%) |
|---|---|
| 4 weeks | 97.2 |
| 2 months | 97.4 |
| 3 months | 95.4 |
| 4 months | 95.8 |
| 5 months | 95.1 |

TABLE 1-continued

Storage life of the liquid formulation according to
the invention of the conidia of *Paecilomyces lilacinus*

| Storage time | Germinated conidia (%) |
|---|---|
| 6 months | 94.1 |
| 7 months | 94.7 |
| 8 months | 93.0 |
| 9 months | 94.1 |
| 10 months | 93.5 |
| 11 months | 92.8 |
| 12 months | 92.3 |

Example 2

A pot test was used to investigate the action of a liquid preparation produced on the basis of *Paecilomyces lilacinus* on the population of the root-knot nematode (*Meloidogyne incognita*) in the soil and also on the nematode-caused symptoms on tomato roots.

A liquid preparation, as in example 1, containing exactly $1 \times 10^{11}$ live fungal conidia per milliliter was used. The pots were each filled with 1000 ml of soil and each inoculated with 5000 eggs and larvae of *Meloidogyne incognita*. To this end, holes were pressed into the soil, and the nematode suspension was pipetted into the holes. The liquid preparation was applied on the day following the inoculation. To this end, 10 milliliters of the liquid preparation were mixed into 10 liters of water. From the resulting conidia suspension, 10 ml were administered to each pot. Thereafter, the pots were watered until the soil was saturated. The applied amount used corresponds to a liquid preparation amount of 0.01 ml per pot or to a conidia concentration of $1 \times 10^9$ conidia per pot.

7 days after the treatment, tomato plants approx. 15 cm in height were planted in the pots. The treatment was repeated a total of 3 times, firstly 3 weeks after planting, and then every 4 weeks. The evaluation of the test was carried out 14 weeks after planting (3 weeks after the last application). As control, an untreated variant was tested in parallel. Both variants, treated and untreated, were assessed using 8 replicates. The result of the test is shown in table 2.

TABLE 2

Effect of a liquid preparation consisting of the conidia
of *Paecilomyces lilacinus* suspended in polyether-
modified trisiloxane (Break-Thru S 240) on the propagation
of *Meloidogyne incognita* and on the nematode-caused
symptoms on the roots

|  | Number of *M. incognita* egg masses per root | Symptoms according to a scoring scheme ranging from 0 to 10* |
|---|---|---|
| Pots treated with the liquid preparation | 49 | 1.2 |
| Untreated pots | 355 | 5.3 |

*Scoring scheme: 0 = no symptoms, 10 = plants dead

Example 3

The fungus *Nomuraea rileyi* was cultured on a suitable solid substrate under axenic conditions. After culturing, the culture substrate with the fungal conidia situated thereon was dried.

The conidia were then separated from the dry culture substrate with the aid of an air-classification and filtration method. At this time, they contained residual moisture of 9.2%. 7 g of the dried conidia powder, which had a concentration of $8.03 \times 10^{10}$ conidia per gram, were suspended in 100 ml with propylene glycol n-butyl ether-modified trisiloxane. The resulting liquid preparation contained $5.62 \times 10^9$ conidia per milliliter and $5.19 \times 10^9$ live conidia per milliliter. This corresponds to a concentration of live conidia in the liquid preparation of 92.35%.

The liquid preparation was incubated at room temperature (20-22° C.), and the germination capacity of the conidia of *Nomuraea rileyi* was determined monthly. To investigate the germination capacity, samples were taken regularly, mixed with water in a ratio of 1:2000, incubated for 5 hours in this mixture, and spread out in 0.1 ml on a suitable agar growth medium. The agar plates were then incubated at 25° C. for 40 hours and then examined under a microscope. In this examination, the number of germinated conidia, which are clearly identifiable by the formation of a germ tube, was determined and related to the number of nongerminated conidia. The results of the counts are shown in table 3.

TABLE 3

Storage stability of the liquid formulation according
to the invention of the conidia of *Nomuraea rileyi*

| Storage time | Germinated conidia (%) |
|---|---|
| 4 weeks | 91.3 |
| 2 months | 91.5 |
| 3 months | 90.3 |
| 4 months | 88.8 |
| 5 months | 89.5 |
| 6 months | 88.1 |
| 7 months | 87.1 |
| 8 months | 85.3 |
| 9 months | 85.9 |
| 10 months | 86.7 |
| 11 months | 84.0 |
| 12 months | 85.2 |

Example 4

In a laboratory test, larvae of *Spodoptera exigua* using a specifically composed diet were kept in small Plexiglas vessels (base: 174 mm$^2$) at a relative air humidity of 75% and a temperature of 26° C.+/−2° C. 5 days after hatching (2nd larval stage), the larvae were treated with the spore product according to the invention. To this end, a liquid preparation containing exactly $5 \times 10^9$ live fungal conidia per milliliter in tripropylene glycol methyl ether-modified trisiloxane was used. To produce the spray suspension, 10 ml or 2 ml of said liquid preparation were mixed into 4 l of water. From the resulting spore suspension, 4 ml were sprayed onto an area of 100 cm$^2$. This corresponds to a spray liquid application amount of 1000 ml or 200 ml of the liquid preparation per hectare mixed into, in both cases, 400 liters of water per hectare. The small vessels in which the larvae were incubated were, at the time of the application, situated on the area over which the spray was applied. The evaluation of the test was carried out 1, 3 and 7 days after the treatment by determining the number of dead larvae and determining the extent of mortality. Overall, 10 larvae per vessel and 3 vessels per test variant were tested.

TABLE 4

Mortality of the larvae of Spodoptera exigua after treatment with a water-dissolved liquid preparation consisting of the conidia of the fungus Nomuraea rileyi suspended in tripropylene glycol methyl ether-modified trisiloxane.

| Treatment | Application amount | Mortality after 1 day | Mortality after 3 days | Mortality after 7 days |
|---|---|---|---|---|
| Untreated variant | 0 | 0.00% | 0.00% | 9.37% |
| Liquid preparation containing the conidia of Nomuraea rileyi | 200 ml/ha | 25.00% | 90.62% | 100.00% |
| Liquid preparation containing the conidia of Nomuraea rileyi | 1000 ml/ha | 68.00% | 100.00% | 100.00% |

LITERATURE

Anonymous (2005): Vom Wirkstoff zum Produkt—Formulierung macht's [From active substance to product—the formulation makes it possible]. KURIER, Das Bayer CropScience Magazin für moderne Landwirtschaft [KURIER, The Bayer CropScience Magazine for Modern Agriculture] 5(1): 6-9

Akbar W, Lord J C, Nechols J R, Loughind T M (2005): Efficacy of Beauveria bassiana for Red Flour Beetle When Applied with Plant Essential Oils or in Mineral Oil and Organosilicone Carriers. Journal of Economic Entomology 98(3): 683-688

Gatarayiha M C, Laing M D, Miller R M (2010): Effects of adjuvant and conidial concentration on the efficacy of Beauveria bassiana for the control of the two spotted spider mite, Tetranychus urticae. Experimental and Applied Acarology 50(3): 217-229

Legaspi J C, Poprawski T J, Legaspi B C Jr. (2000): Laboratory and field evaluation of Beauveria bassiana against sugarcane stalkborers (Lepidoptera: Pyralidae) in the lower Rio Grande Valley of Texas. J Econ Entomol. 93(1): 54-9

Wekesa V W, Maniania N K, Knapp M, Boga H I (2005): Pathogenicity of Beauveria bassiana and Metarhizium anisopliae to the tobacco spider mite Tetranychus evansi. Experimental and Applied Acarology 36(1-2): 41-50

The invention claimed is:

1. A liquid preparation for biological plant protection comprising a suspension, said suspension comprising (i) spores or conidia of Paecilomyces lilacinus or Nomuraea rileyi and (ii) a polyether-modified trisiloxane in an amount that is effective for long storage life, wherein at least 85% of the spores or conidia of the Paecilomyces lilacinus or the Nomuraea rileyi are capable of germination after storage for four weeks.

2. The liquid preparation as claimed in claim 1, wherein said polyether-modified trisiloxane comprises Break-Thru® S 240, which corresponds to CAS No. 134180-76-0.

3. The liquid preparation as claimed in claim 1, wherein said trisiloxane has been modified with at least one of
propylene glycol n-butyl ether (PnB),
dipropylene glycol n-butyl ether (DPnB),
dipropylene glycol methyl ether acetate (DPMA),
tripropylene glycol methyl ether (TPM),
propylene glycol methyl ether (PM),
propylene glycol methyl ether acetate (PMA),
dipropylene glycol methyl ether (DPM), and/or
tripropylene glycol monomethyl ether.

4. The liquid preparation as claimed in claim 1, wherein the Paecilomyces lilacinus or the Nomuraea rileyi has an antagonistic and/or hyperparasitic action directed against a plant disease-causing organism.

5. The liquid preparation as claimed in claim 1, wherein the Paecilomyces lilacinus or the Nomuraea rileyi has a resistance-inducing action and/or stress tolerance-inducing action which manifests on a plant and/or a nutrient availability-increasing action.

6. A method for producing the liquid preparation of claim 1, comprising culturing the Paecilomyces lilacinus or the Nomuraea rileyi and then suspending in a polyether-modified trisiloxane in an amount that is effective for long storage life, wherein at least 85% of the spores or conidia of the Paecilomyces lilacinus or the Nomuraea rileyi are capable of germination after storage for four weeks.

7. The method as claimed in claim 6, wherein said polyether-modified trisiloxane comprises Break-Thru® S 240, which corresponds to CAS No. 134180-76-0.

8. The method as claimed in claim 6, wherein fungal material is processed by milling and/or dispersion.

9. The method as claimed in claim 8, wherein said fungal material is isolated after processing by sieving, filtration, air-classification and/or centrifugation.

10. A liquid preparation as claimed in claim 1 capable of being mixed into soil, applied to/on a plant, and/or as seed treatment.

11. The liquid preparation as claimed in claim 1, wherein at least 85% of the spores or conidia of the Paecilomyces lilacinus or the Nomuraea rileyi are capable of germination after storage for four weeks at room temperature.

12. The method as claimed in claim 6 wherein at least 85% of the spores or conidia of the Paecilomyces lilacinus or the Nomuraea rileyi are capable of germination after storage for four weeks at room temperature.

* * * * *